(12) United States Patent
Lin et al.

(10) Patent No.: US 7,410,811 B2
(45) Date of Patent: Aug. 12, 2008

(54) ANALYTICAL METHOD AND DEVICE UTILIZING MAGNETIC MATERIALS

(75) Inventors: Yuh Jiuan Lin, Taipei County (TW); Kun Feng Lee, Kaohsiung County (TW); Chi Min Chau, Taichung County (TW); Hui Ju Cho, Changhua County (TW)

(73) Assignee: Industrial Technology Research Institute, Hsinchu (TW)

( * ) Notice: Subject to any disclaimer, the term of this patent is extended or adjusted under 35 U.S.C. 154(b) by 189 days.

(21) Appl. No.: 11/320,659

(22) Filed: Dec. 30, 2005

(65) Prior Publication Data
US 2006/0286563 A1 Dec. 21, 2006

(30) Foreign Application Priority Data
Jun. 21, 2005 (TW) .............................. 94120567 A

(51) Int. Cl.
*G01N 33/553* (2006.01)
(52) U.S. Cl. ................... 436/526; 310/311; 310/313 R; 435/6; 436/524; 436/525; 436/527; 436/172; 436/805

(58) Field of Classification Search ....................... None
See application file for complete search history.

(56) References Cited

U.S. PATENT DOCUMENTS

2003/0012693 A1* 1/2003 Otillar et al. .................. 422/58
2005/0082944 A1* 4/2005 Thompson et al. .......... 310/318

OTHER PUBLICATIONS

Li et al, "Piezoelectric immunosensor based on magnetic nanoparticles with simple immobilization procedures", Analytica Chimica Acta 481(2), 2003, pp. 191-198.*

* cited by examiner

*Primary Examiner*—Christopher L Chin
(74) *Attorney, Agent, or Firm*—Bacon & Thomas PLLC

(57) ABSTRACT

The present invention relates to an analytical method and device utilizing magnetic materials and acoustics sensor. The invention employs a magnetic material modified with specific recognizable molecules to capture a substance in a sample and provides an external magnetic field to draw the magnetic material to an sensing region of an acoustics sensor, and then converts an effect occurred on a surface of the sensing region to an amount of the substance in the sample, wherein the effect is caused by a contact of the surface with the magnetic material and the substance.

9 Claims, 10 Drawing Sheets

ANALYTICAL METHOD AND DEVICE UTILIZING MAGNETIC MATERIALS

BACKGROUND OF THE INVENTION

1. Field of the Invention

The present invention relates to an analytical method and device utilizing magnetic materials and acoustics sensor, in particular, an analytical method and device that combines the use of magnetic materials and mass-sensitive sensor.

2. Description of the Related Art

There are in general two approaches to assaying a substance in a sample. One is utilizing separation technique, such as solvent extraction, condensation, precipitation, or chromatography to purify the target substance and then quantify its content. The other is utilizing reaction specificity to directly measure the amount of a specific substance in a complex sample. The process of purification-quantification is prone to result in loss of bioactivity and error, especially when the process is sophisticated and protracted. Thus assay techniques nowadays are mostly developed towards the specific reaction approach. The use of biosensor is one of the examples.

A biosensor typical consists of recognizable molecules, transducer and signal processor. The recognizable molecules are located on the surface of a sensing region of transducer to contact the target substance and react with it. Thus recognizable molecules must possess specificity for the target substance to enhance sensor selectivity. Commonly used recognizable molecules include biological tissue, microorganism, organelle, cell receptor, enzyme, antigen and antibody.

The function of a transducer is to convert changes in the physical quantity or chemical quantity of recognizable molecules after its reaction with the target substance into electronic signals. Physical quantity or chemical quantity could be optically, mass, thermochemically, electrochemically or magnetically. For example, in a biosensor system using enzyme as recognizable molecules, the reaction between enzyme and substrate is highly selective, and heat, changes in pH or absorption band, or other chemical substances would occur in the reaction process. Coupled with a proper transducer (e.g. thermocouple, electrode, photon counter, etc.), the changes in the process are converted into current signals, which are then read and process by a signal processor to determine the properties and content of the target substance. In the same way, when the quartz crystal microbalance (one kind of acoustics sensing elements) is used as a transducer, the binding of target substance to recognizable molecules coated on the surface of quartz crystal causes mass change on it, which leads to changes in the frequency of quartz crystal and allows measurement of the content of target substance. But to modify recognizable molecules on the surface of the sensing region of transducer usually need troublesome surface treatment and protein immobilization technics, and result in poor detection sensitivity and signal reproducibility. To render the use of highly sensitive acoustics sensor more efficient and free of restrictions, magnetic material modified with recognizable molecules is incorporated in the development of related techniques.

A prior art (U.S. Pat. No. 6,294,342) utilizes a magnetically responsive reagent that can recognize the target substance and a mobile solid phase reagent to determine the presence or amount of target substance contained in a sample by measuring the response to the magnetic field of the magnetically responsive reagent, or that of the mobile solid phase reagent. This prior art requires the combined use of magnetically responsive reagent and mobile solid phase reagent to produce measurable effect. Such effect is weight change caused by the changes in the attraction or repulsion between magnet and magnetic bead. Also, the method disclosed in the prior art is sensitive only to the level of microgram ($\mu g$).

Another prior art (U.S. Pat. No. 5,660,990) discloses the use of a capture agent to capture the target substance and then bind to a signal producing agent, and signals produced by the signal producing agent are detected and measured. In this technique, the use of additional agents adds more steps to the process and restrictive binding conditions tend to result in error. U.S. Pat. No. 6,342,396 discloses a method of immobilizing receptor on the surface of a capturing means to capture recognizable particles in a test sample. In this technique, the use of a specific receptor on the capturing means limits its application to specific analyte, or the surface of capturing means needs to be replaced for it to analyze other substances. Thus the technique lacks the value of general application.

This invention aims to provide a biosensor device and analytical method that are more sensitive, simpler and don't need use extra labeling materials.

SUMMARY OF THE INVENTION

In addressing the drawbacks of prior art, the present invention provides an analytical method and device, which utilizes recognizable molecules modified magnetic material to capture the target substance in a sample and provides an external magnetic field to draw the magnetic material to an sensing region of an acoustics sensor, and then converts the effect occurred on a surface of the sensing region to an amount of the target substance in the sample.

An object of the present invention is to provide a method for analyzing a target substance in a sample, comprising the steps of: a) providing a magnetic material having recognizable molecules on its surface to capture the target substance in a sample; b) adding the magnetic material to a sample for the recognizable molecules thereon to capture target substance in the sample; c) using a magnetic field to draw the magnetic material to the surface of an sensing region of an acoustics sensor to produce the change of acoustic effect thereon; and d) converting the acoustic effect into the amount of the target substance in the sample.

Another object of the present invention is to provide a device for analyzing a target substance in a sample, comprising: a reaction cell having a space for the injection of sample; a magnetic material having recognizable molecules on its surface to capture target substance in the sample; a magnetic field generator to provide an external magnetic field for the magnetic material in the reaction cell; and an acoustics sensor having an sensing region exposed in the reaction cell; wherein the device utilizes the external magnetic field provided by the magnetic field generator to draw the magnetic material and the target substance captured to the surface of the sensing region of acoustics sensor, and result in the change of acoustic effect thereof is converted to obtain the amount of target substance in the sample.

The device according to the invention further contains an optical sensor to detect the magnetic material.

In one embodiment of the device for analyzing target substance in a sample, the reaction cell is a vessel for static storage of sample therein. In another embodiment, the reaction cell is a channel that allows the flowing of sample therein.

The magnetic separation technique disclosed in this invention does not require the use of solvent extraction, condensation, precipitation or chromatography to achieve the separation and quantification of substance. When applied to biosensor system, the invention rids the difficulty of surface modification of acoustics sensor and provides a means to preseparate and prepurify the sample so as to reduce the interference of non-analytes in the detection and quantification process.

DETAILED DESCRIPTION OF THE INVENTION

The method for analyzing target substance in a sample utilizing magnetic materials according to the invention first provides a magnetic material. The term "magnetic material" means a material that can be led and moved by an external magnetic field, including magnetic particles, magnetic nanoparticles and superparamagnetic nanoparticles. To capture the target substance in a sample, the surface of the magnetic material is modified with recognizable molecules. The recognizable molecules, including compound, antigen, antibody, receptor, ligand, enzyme, protein, peptide and nucleic acid, are selected based on the properties of the target substance. The magnetic material carrying recognizable molecules thereon is added to the sample. After the recognizable molecules on the magnetic material capture the target substance in the sample, a magnetic field is used to draw the magnetic material to a surface of an sensing region of an acoustics sensor and produce the change of acoustic effect thereon. The acoustics sensor includes but is not limited to quartz crystal microbalance (QCM), surface acoustic wave (SAW) device, flexural plate wave (FPW) sensor, acoustic plate mode (APM) device, and micro/nano cantilever beam. When the complex of magnetic material and target substance gets in contact with the sensing region of acoustics sensor, the surface of sensing region undergoes deformation change, change of resonance frequency shift, or change of acoustic wave signal. Different concentrations of the target substance would cause different levels of acoustic effect change. Thus the amount of the target substance in the sample may be obtained by converting the acoustic effect produced response.

Some magnetic materials itself or doped with light sensitive component, can emit or absorb different wavelengths of light. For instance, they can emit or absorb visible light, infrared or ultraviolet light, or emit fluorescence, phosphorescence, or luminescence. And those magnetic materials would produce different level of light emission or light absorption after they capture different amounts of target substance. Thus aside from using acoustics sensor to detect acoustic effect, optical sensor can be used to detect changes in light emission and absorption. More so, the surface of magnetic material can be further modified with signal molecules to enhance the characteristics of light emission or light absorption, so that the effect produced by the binding of target substance and magnetic material becomes more pronounced.

Figure 1:
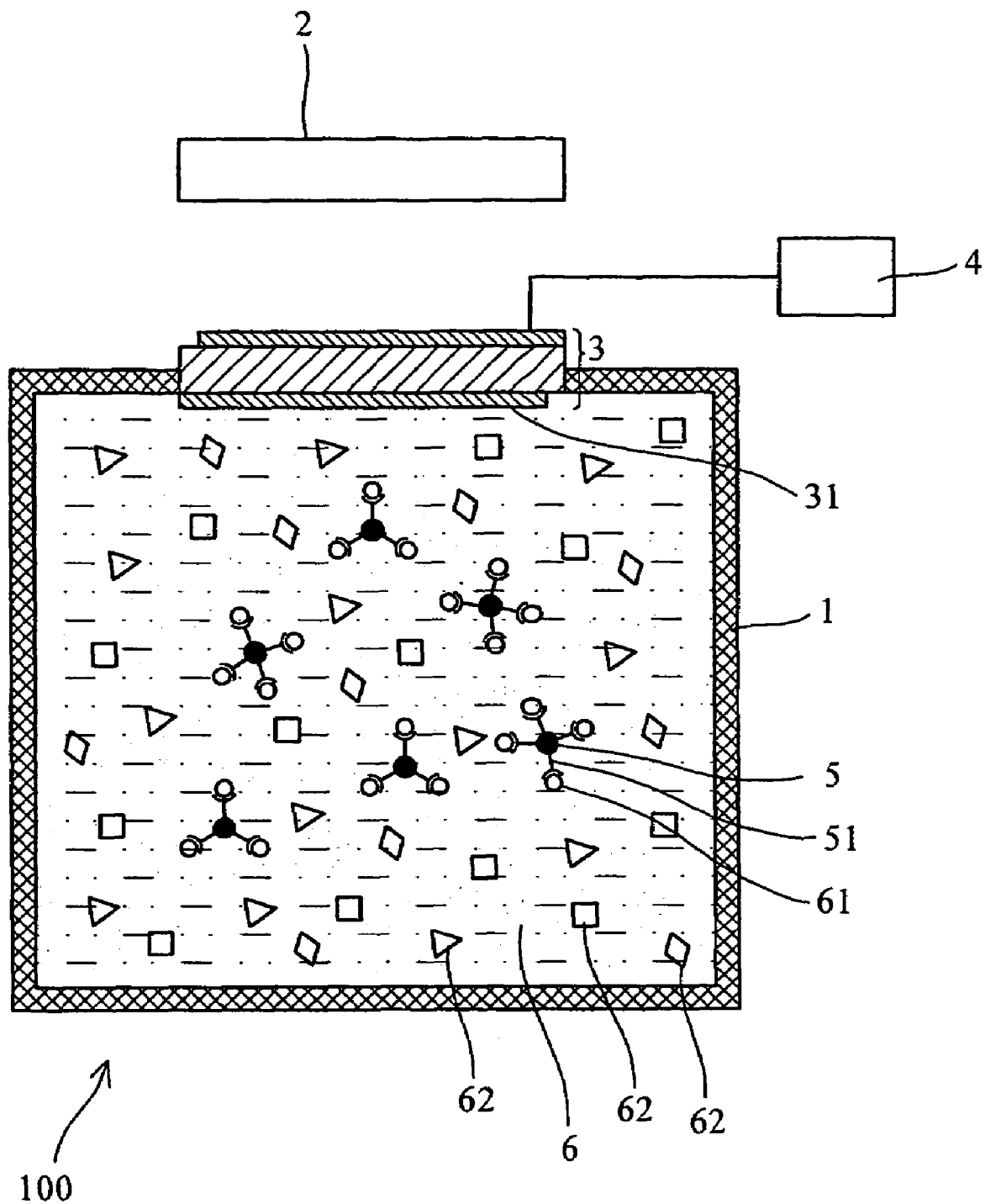
FIG. 1 is a schematic view of the analytical device according to the invention, in which the magnetic field generator does not provide an external magnetic field and the reaction cell is a vessel.

An embodiment of the device 100 for analyzing a target substance in a sample according to the invention as shown in FIG. 1 comprises a reaction cell 1, a magnetic field generator 2, an acoustics sensor 3, a signal processor 4, and a magnetic material 5. The reaction cell 1 is a vessel for static storage of test sample 6 therein. The magnetic material 5 is mixed and distributed in the test sample 6. The magnetic material 5 is magnetic particles, magnetic nanoparticles or superparamagnetic nanoparticles modified with recognizable molecules 51, micrometer or nanometer in size, and able to selectively capture target analyte 61 in the test sample 6. Recognizable molecules 51 that modify the surface of magnetic material 5 include but are not limited to compound, antigen, antibody, receptor, ligand, enzyme, protein, peptide, and nucleic acid that possess the characteristics of recognizing the target analyte 61. The techniques for modifying the surface of magnetic material 5 with recognizable molecules 51 are those commonly used in the field. For example, if the magnetic material 5 is a hydroxyl ion-oxide particle, its hydroxy group can form chemical bond with alkoxy silane, and other functional groups on alkoxy silane can form chemical bond with recognizable molecules 51 to achieve modification. In addition, dextrin can also be surface modified under similar reactions. The acoustics sensor 3 includes but is not limited to quartz crystal microbalance (QCM), surface acoustic wave (SAW) device, flexural plate wave (FPW) sensor, acoustic plate mode (APM) device, and micro.nano cantilever beam. In an embodiment of the invention, a QCM sensor is used. Said QCM sensor has an sensing region 31 exposed in reaction cell 1, which is disposed in a region to which magnetic material 5 is drawn when the magnetic field generator 2 provides an external magnetic field, including the bottom, periphery, and top of reaction cell. The sensing region is preferably located at the top of reaction cell 1 so as to reduce the gravity-induced precipitation of substances other than the target analyte 61 (i.e. non-analytes 62) on the sensing region 31, which tends to affect the accuracy of analysis. The magnetic field generator 2 is a device that can provide an external magnetic field for the reaction cell 1, including but not limited to sensing coil or magnet.

Figure 2:
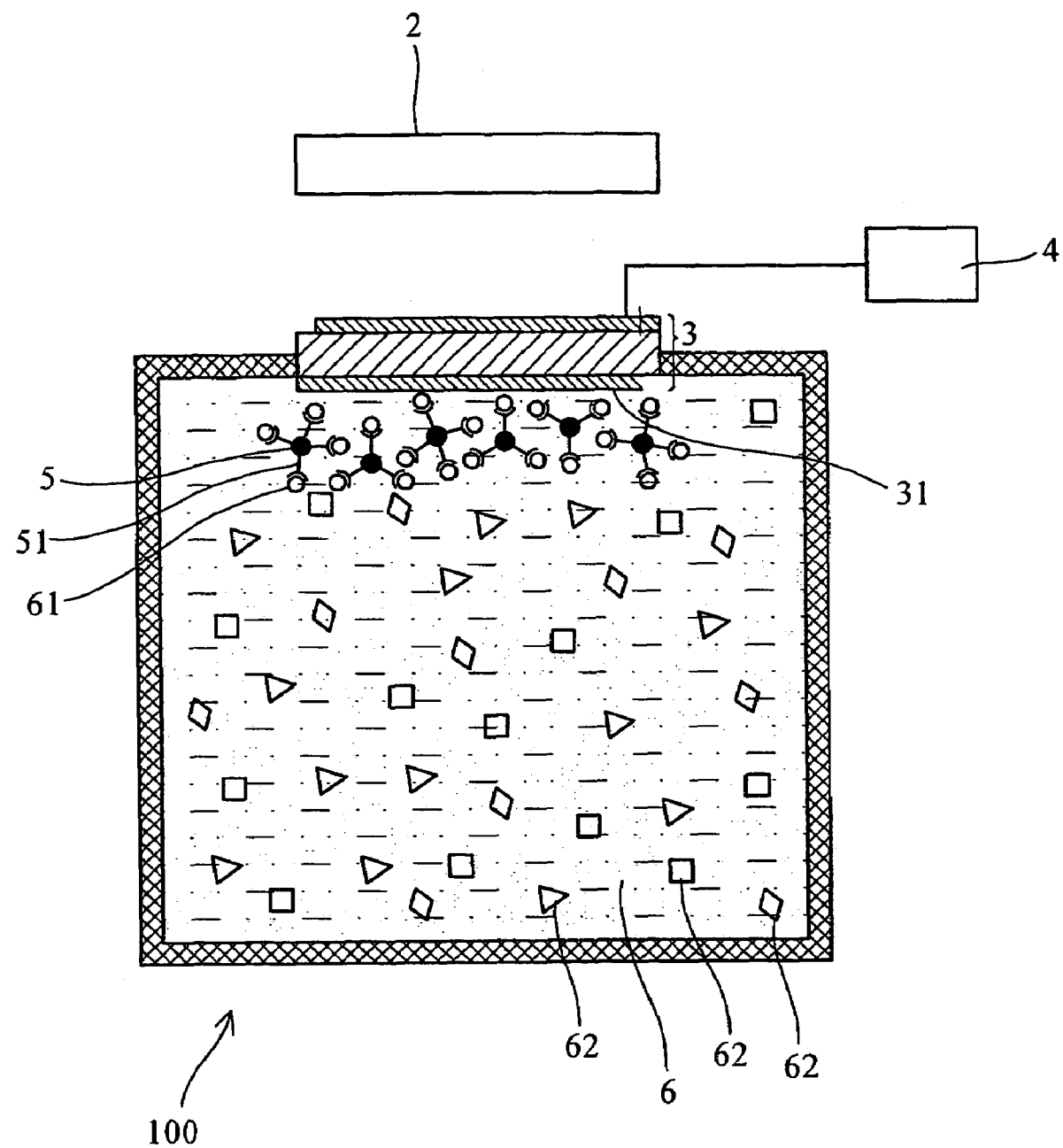
FIG. 2 is a schematic view of the analytical device according to the invention, in which the magnetic field generator provides an external magnetic field and the reaction cell is a vessel.

Referring to FIG. 2, when the magnetic field generator 2 provides an external magnetic field to draw the magnetic material 5 to the surface of sensing region 31, the analyte 61 captured by magnetic material 5 will determine the degree of effect produced on the sensing region 31. Such effect includes but is not limited to changes in the average quantity of magnetic material, the aggregation effect, changes in viscosity, changes in density, changes in magnetic force, changes in temperature, and changes in charge of magnetic material. The occurrence of the aforesaid effect will cause the acoustics sensor 3 to undergo changes, including but not limited to changes in deformation, resonance frequency shift, and acoustic wave signal. The signal processor 4 analyzes the magnitude of changes in acoustics sensor 3 and converts it into the amount of target analyte 61 in the test sample 6. The signal processor 4 may be a separate apparatus or integrated to the acoustics sensor 3.

Figure 3:
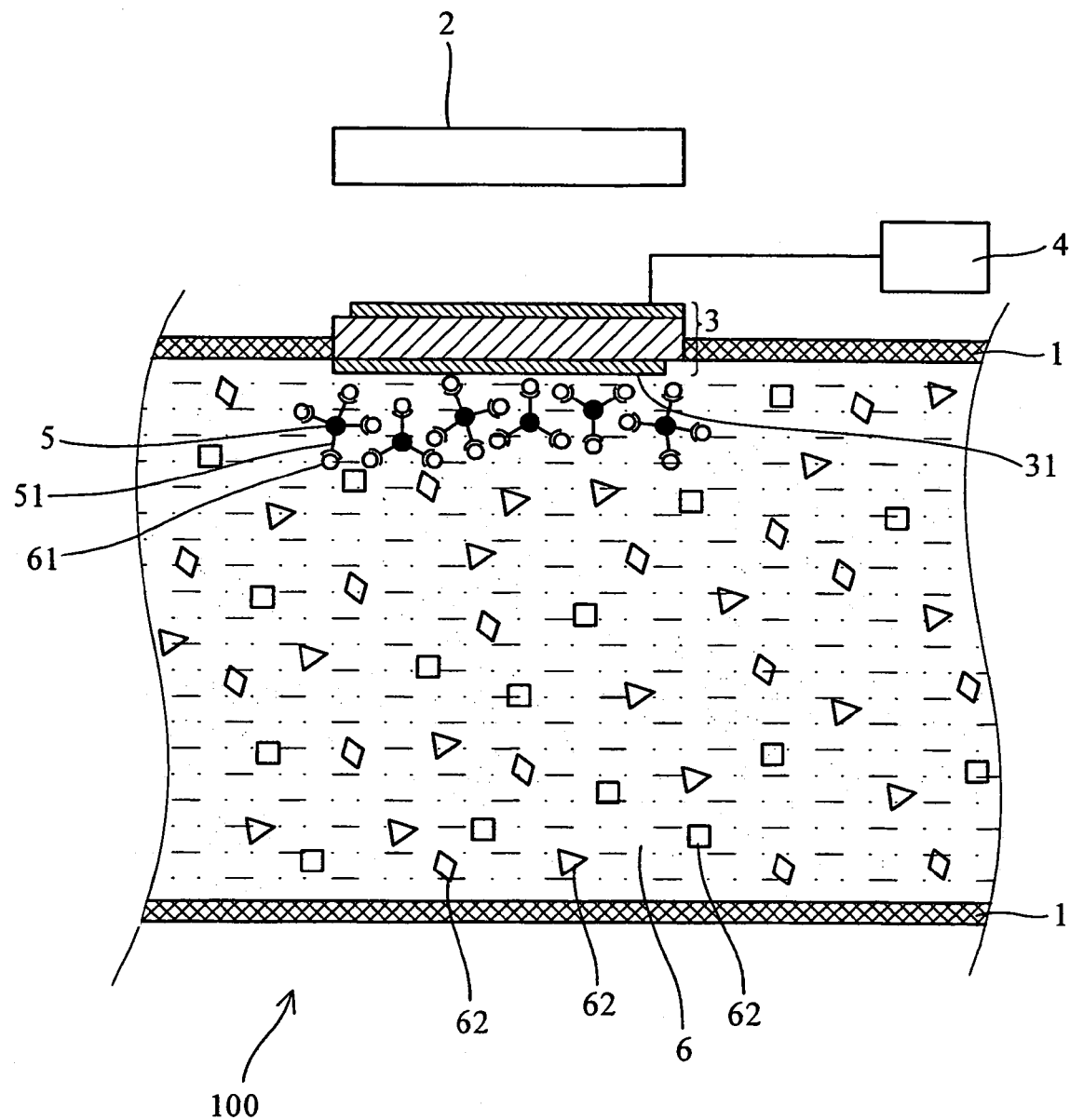
FIG. 3 is a schematic view of the analytical device according to the invention, in which the magnetic field generator provides an external magnetic field and the reaction cell is a channel.

FIG. 3 shows another embodiment of the invention, where the reaction cell 1 is a channel that allows dynamic flowing of test sample 6 in the reaction cell 1 to achieve the purpose of continuous assay. When the magnetic material 5 mixed in the test sample 6 to capture the target analyte 61 passes through the external magnetic field provided by the magnetic field generator 2, it will be drawn to the surface of an sensing region 31 of the acoustics sensor 3 exposed in reaction cell 1. At this time, the analytes 61 and non-analytes 62 in the test sample 6 are separated, and magnetic material 5 that amasses in the sensing region 31 would cause changes in acoustics sensor 3. Signal processor 4 can convert the changes occurred in acoustics sensor 3 into the amount of analyte 61 in the test sample 6.

Figure 4:
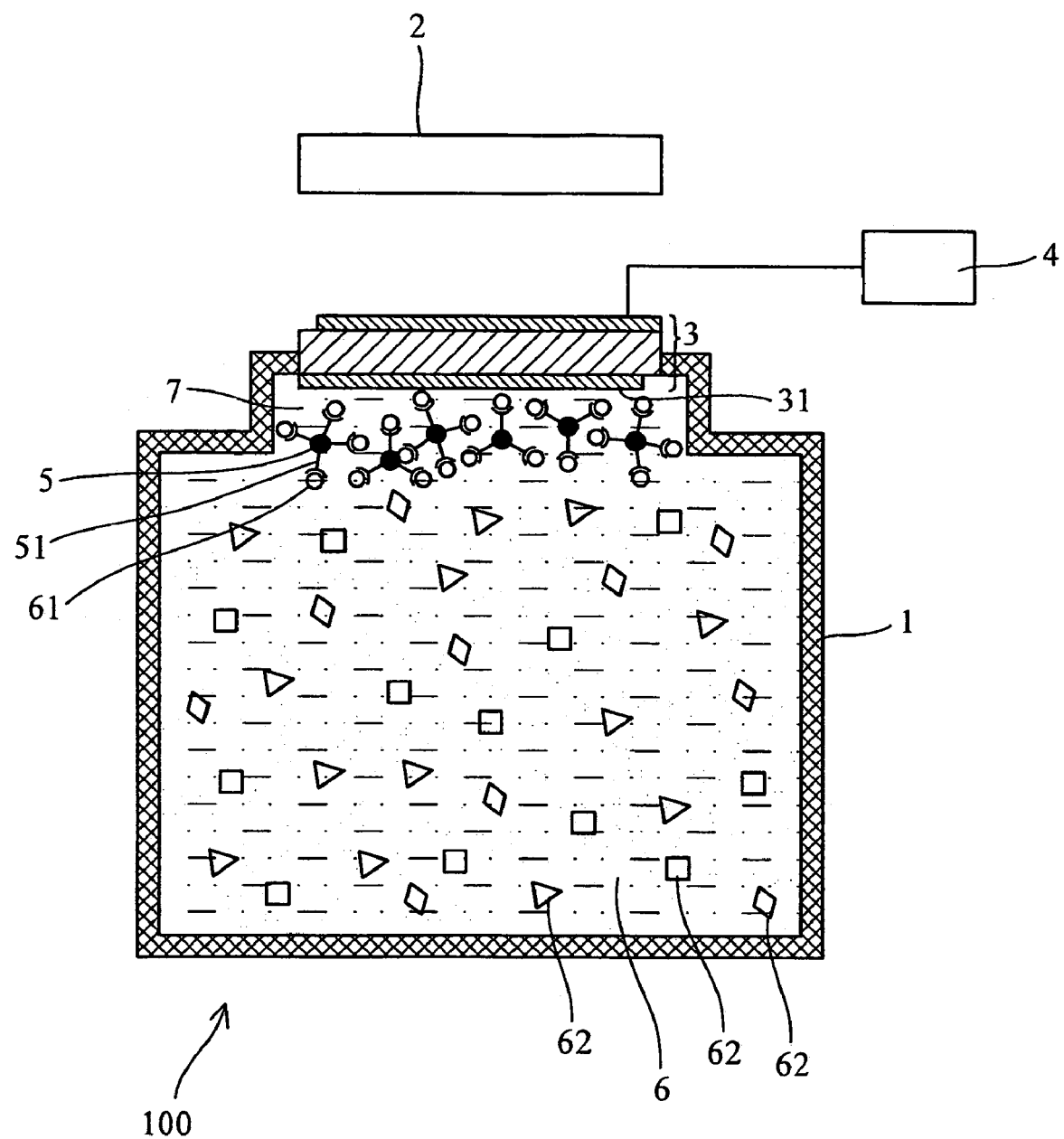
FIG. 4 is a schematic view of the analytical device according to the invention, in which the reaction cell is a vessel with a magnetic material collection zone.
Figure 5:
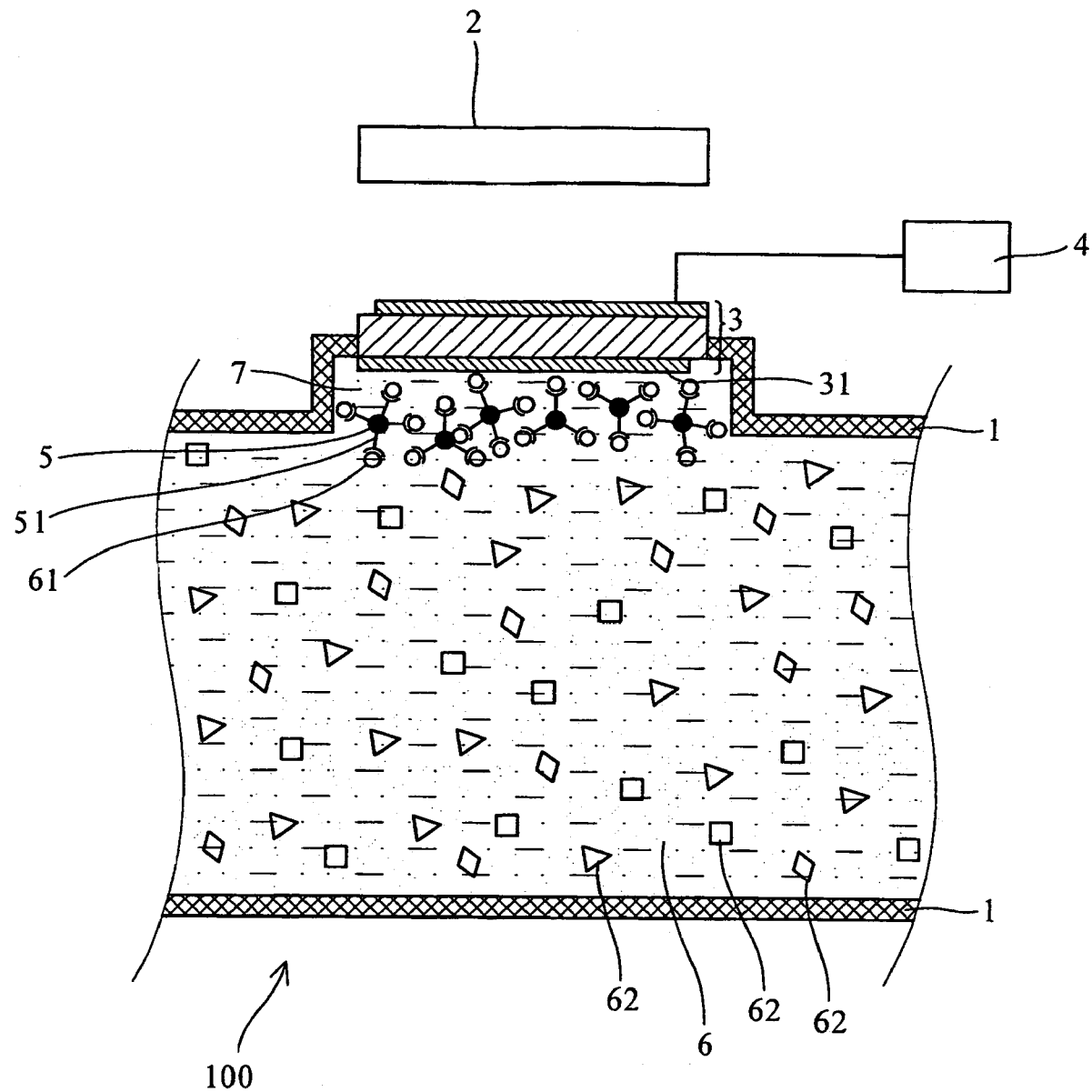
FIG. 5 is a schematic view of the analytical device according to the invention, in which the reaction cell is a channel with a magnetic material collection zone.

The device 100 for analyzing target substance in a sample according to the invention further comprises a magnetic material collection zone 7. As shown in FIG. 4 and FIG. 5 (FIG. 4 shows the device in FIG. 2 that is further added with a magnetic material collection zone 7, and FIG. 5 shows the device in FIG. 3 added with a magnetic material collection zone 7), the arrangement of the magnetic material collection zone 7 is to enhance the concentration of magnetic material 5 on the surface of sensing region 31 when it is drawn and aggregated under the influence of an external magnetic field. By augmenting the effect on the surface of sensing region 31, changes occurred in acoustics sensor 3 are enlarged and signals detected by signal processor are also magnified. Consequently, the amount of the analyte 61 in the test sample 6 obtained thereof is more accurate.

Figure 6A:
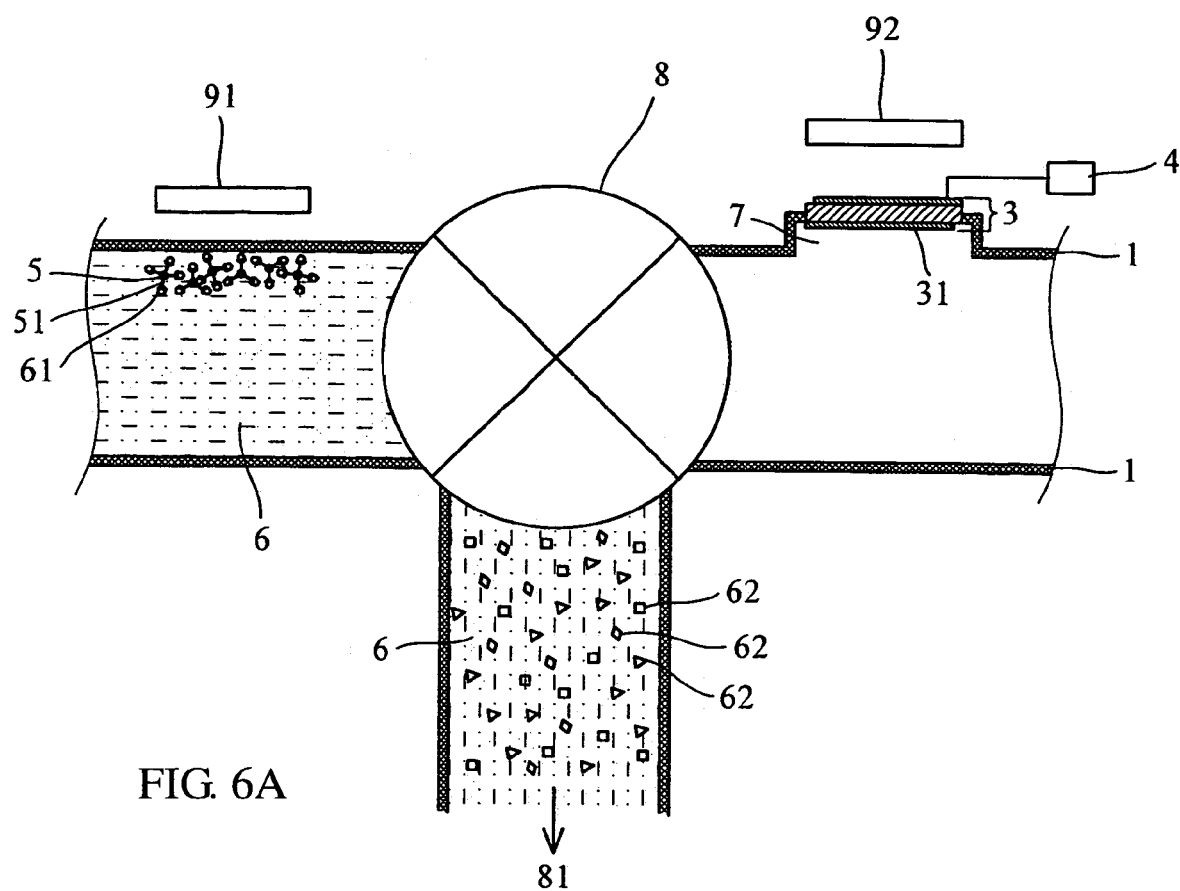
FIG. 6A and FIG. 6B are schematic views of the analytical device according to the invention, in which the reaction cell is a channel with a regulating valve to control the direction of fluid flow in the channel.
Figure 6B:
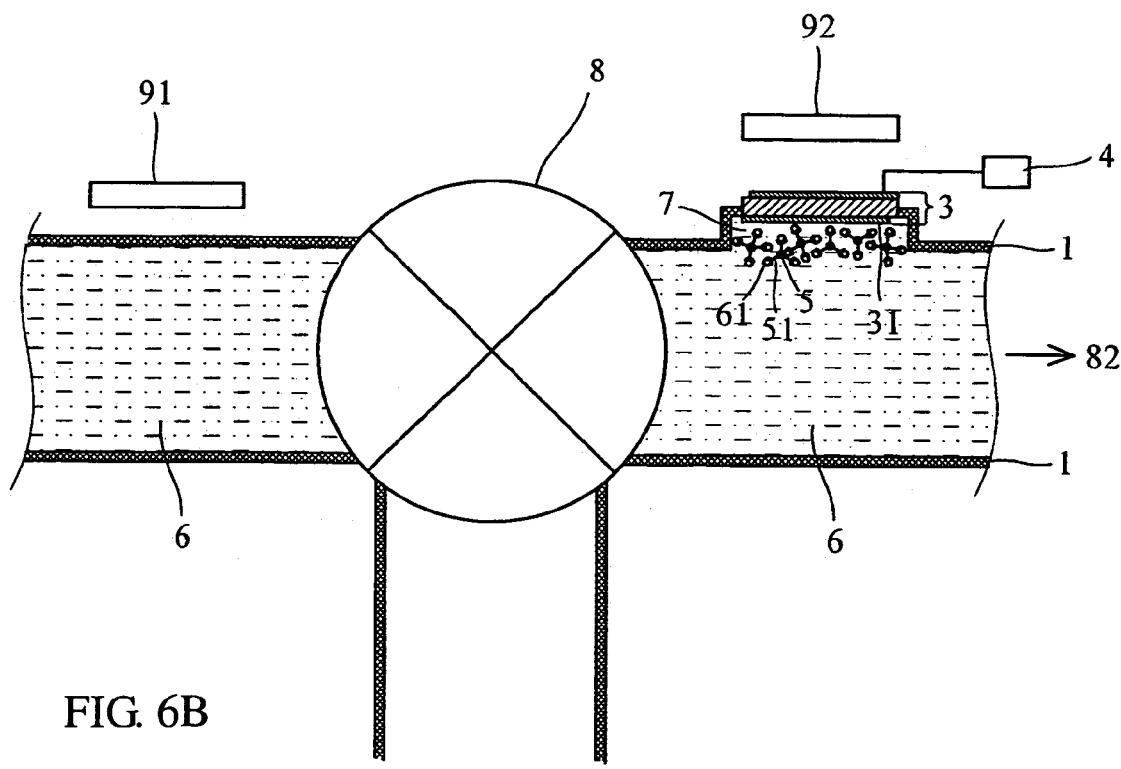

Another embodiment of the invention is shown in FIG. 6A and FIG. 6B. In FIG. 6A, the mixture of magnetic material 5 and test sample 6 first flows through a magnetic field created by an magnetic field generator 91. At this time, magnetic material 5 that has captured the target analyte 61 would be retained in the magnetic field, while non-analytes 62 in the test sample 6 would continue to pass through a regulating value 8 towards the direction of pathway 81 without being subject to analysis.

Prior to adjusting the regulating valve 8, magnetic material 5 retained in the magnetic field may be washed to remove non-analytes 62 that might affect the accuracy of subsequent analysis. Next, regulating valve 8 is adjusted to guide the flow of fluid from pathway 81 towards pathway 82. At this time, the magnetic field generator 91 is turned off, and the magnetic material retained in the magnetic field starts to flow due to the disappearance of magnetic field and enters pathway 82 through the regulating valve 8. Under the influence of magnetic field created by magnetic field generator 92, the magnetic material is drawn to the surface of sensing region 31 of acoustics sensor 3. As such, signal processor retrieves signal of changes in the acoustics sensor 3 and converts it into the amount of target analyte 61 in test sample 6.

The advantages of the present invention are further depicted with the illustration of examples, but the descriptions made in the examples should not be construed as a limitation on the actual application of the present invention.

EXAMPLE 1

The Effect of Magnetic Particles on Acoustics Sensor Under an External Magnetic Field In this example, self-synthesized magnetic ion-oxide nanoparticles (average particle size of 10 nm; concentration: 20 µg/ml), coupled with flow-injection (flow rate: 160 µl/ml) quartz crystal microbalance (QCM) system were used. Magnetic field was supplied by a magnet (the strength of magnetic field to which the surface sensing region of the acoustics sensor is exposed was 100 mT). The experimental results are depicted in FIG. 7.

Figure 7:
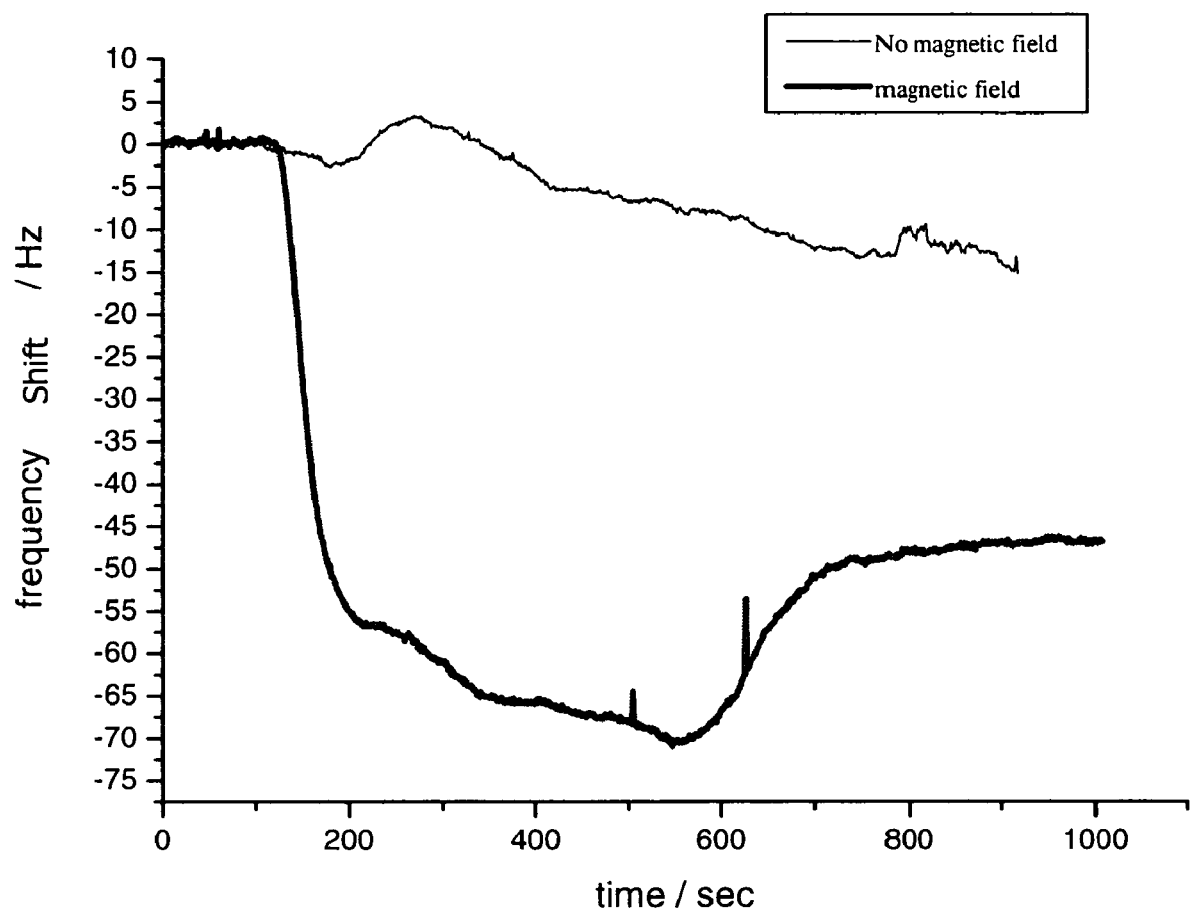
FIG. 7 is a graph illustrating the effects of magnetic materials on acoustics sensor with and without the presence of an external magnetic field.

As shown in FIG. 7, the frequency shift caused by magnetic nanoparticles was 13 Hz in the absence of an external magnetic field, and increased to 46 Hz in the presence of an external magnetic field. This result demonstrates that under the action of an external magnetic field, magnetic particles would attach to the sensing region of QCM sensor, causing the change of piezoelectric effect in the quartz crystal and changing its oscillation frequency.

EXAMPLE 2

The Effect of Protein Modified Magnetic Particles on Acoustics Sensor Under an External Magnetic Field The purpose of this example is in order to evaluate the feasibility of present invention in biochemical detection assay. The experimental apparatus and magnetic materials in this example is the same as that in Example 1, and the results are illustrated in FIG. 8.

Figure 8:
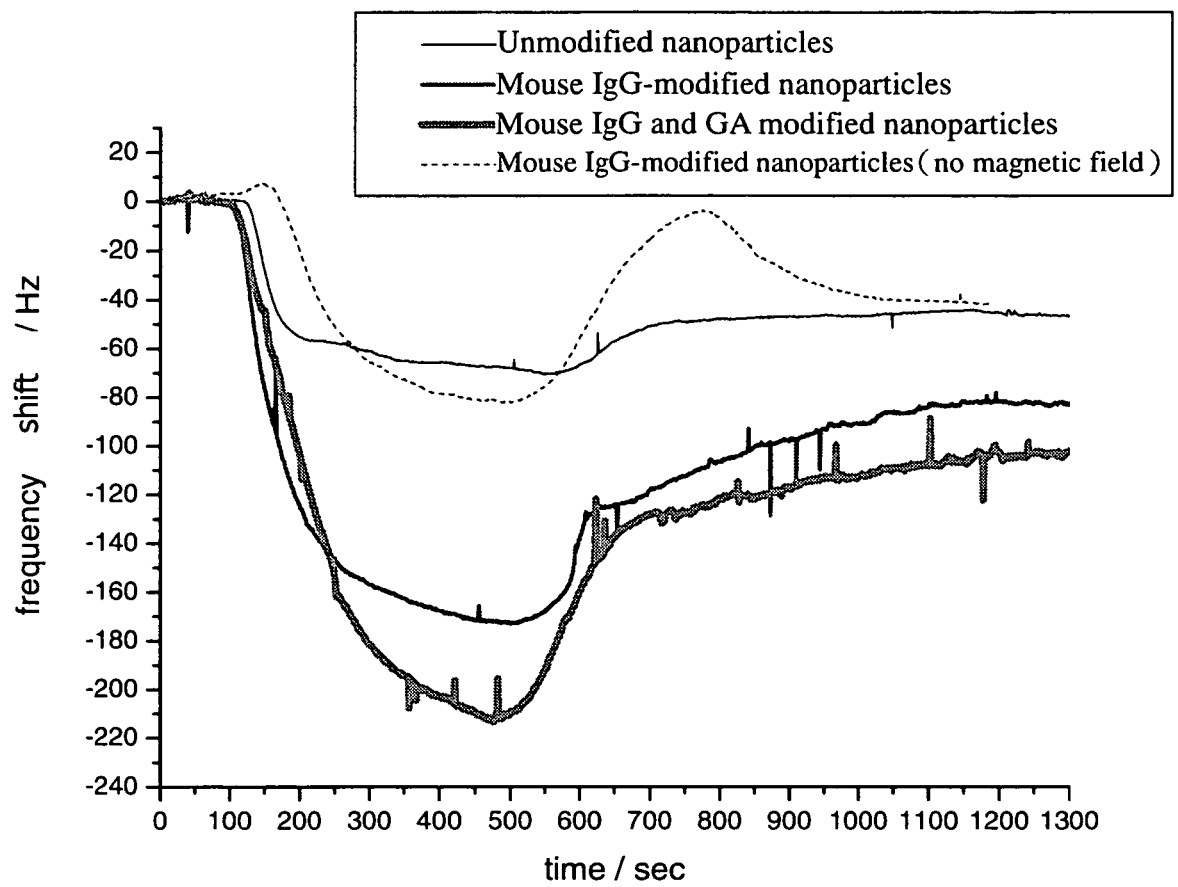
FIG. 8 is a graph illustrating the effects of different magnetic materials under an external magnetic field on acoustics sensor.

As shown in FIG. 8, the frequency shift caused by mouse IgG conjugated magnetic nanoparticles was 41 Hz in the absence of an external magnetic field and rose to 82 Hz in the presence of an external magnetic field. However, after addition of 1.25% glutaraldehyde (GA) (the GA could react with the amine groups of mouse IgG), the measured frequency shift in the presence of an external magnetic field further increased to 103 Hz. This outcome indicates that biomolecules modified magnetic material would cause changes in the oscillation frequency of QCM sensor before and after it captured the target analyte, thereby validating the technical concept of the present invention. The changes in the QCM oscillation frequency may be converted by a signal processor into the amount of target analyte.

EXAMPLE 3

Experiment on the Detection Mechanism of Micro-Size Magnetic Material

This example further examines the feasibility of using micrometer sized magnetic particles in this invention. This example also takes into account the issue of possible non-specific binding of protein to the surface of acoustics sensor. Thus prior to the detection, the surface of acoustics sensor was coated with bovine serum albumin (BSA, concentration: 10 mg/ml) to isolate non-binding proteins in sample, the isolate efficiency could reach 90%.

Figure 9:
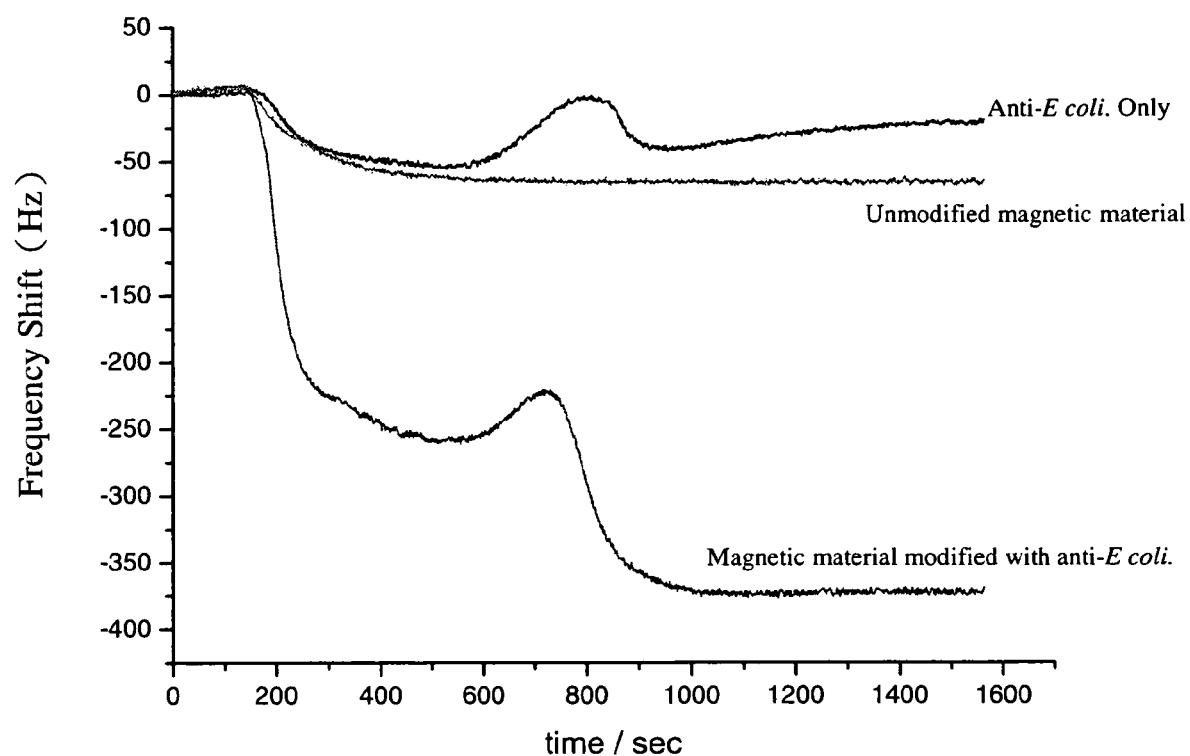
FIG. 9 is a graph illustrating the effects of magnetic materials with different situation of surface on excluded non-specific binding treated acoustics sensor under an external magnetic field.

This example employed magnetic polymer particles supplied by Dynal Biotech (average particle size of 2.8 µm; concentration: 67 µg/ml), coupled with flow-injection (flow rate: 50 µl/ml) quartz crystal microbalance (QCM) system. Magnetic field was also supplied by a magnet (the intensity of magnetic field to which the surface sensing region of the acoustics sensor is exposed was 100 mT). The results as shown in FIG. 9 indicate that in the presence of an external magnetic field, the effect produced by magnetic material modified with anti-*E. coli* (modification conditions: 80 μg/ml anti-*E. coil*+67 μg/ml magnetic material were agitated for about 1.5 hours) was 320 Hz higher than the use of magnetic material without the modification of anti-*E. coil*.

EXAMPLE 4

Application in Immunoassay

Figure 10:
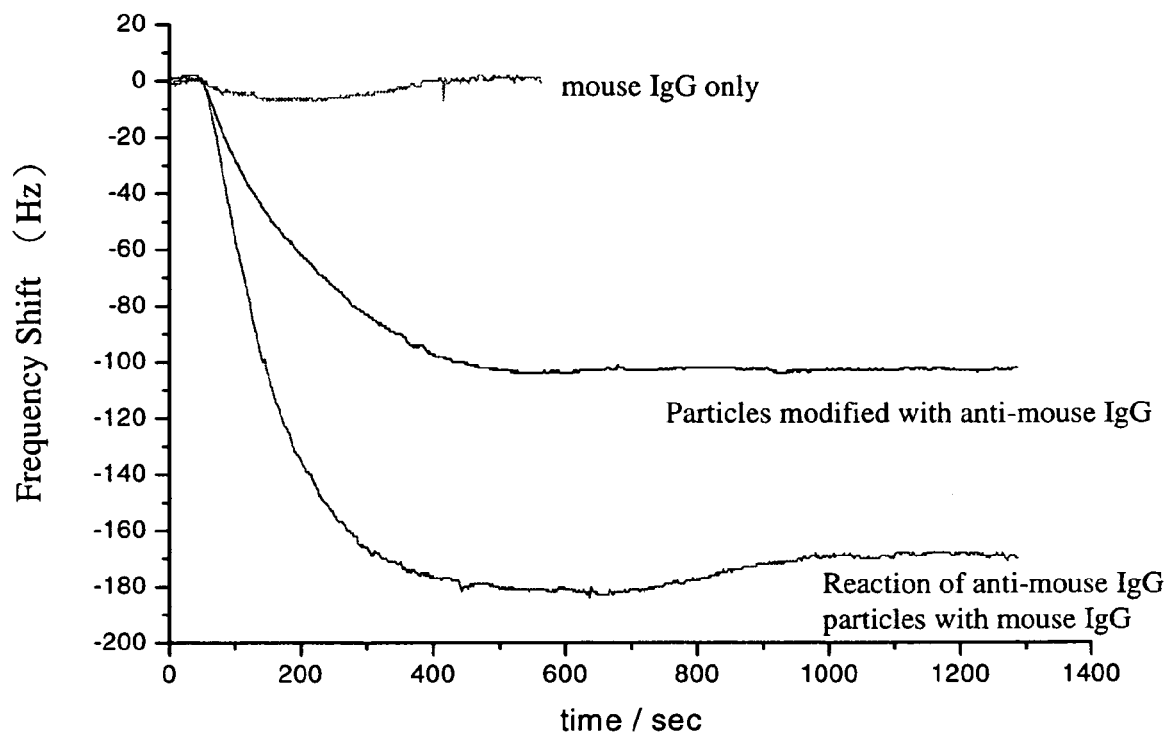
FIG. 10 is a graph illustrating the effect of antibodies coated magnetic material on acoustics sensor under an external magnetic field after capturing the target analytes.

This example utilized magnetic particle modified with anti-mouse IgG (supplied by Dynal Biotech; average particle size of 2.8 μm, concentration: 67 μg/ml) to assay the immunoglobulin of mouse (concentration: 180 μg/ml). The experimental apparatus is the same as that in Example 3, where the surface of acoustics sensor was coated with BSA. The magnetic material modified with anti-mouse IgG was mixed with mouse immunoglobulin for about 1.5 hours before being injected into the channel for assay. FIG. 10 shows the difference of about 70 Hz in frequency change before and after the reaction, which demonstrates the applicability of the present invention in immunoassay.

In summary, the analytical method and device disclosed herein utilizes modified magnetic particles to capture target substance in a sample and provides an external magnetic field to draw the magnetic material to an sensing region of an acoustics sensor. Thus the analytical method and device herein offers a magnetic particle separation technique and the advantages of simple, fast operation, little interference to biomolecules or analyte of interest, and inexpensive assay. Coupled with the high sensitivity of biosensor, it provides an instant assay and quantification technique for trace-amount substances and may be applied extensively in the fields of medicine, environment, and food analysis as trace analysis sensor in diagnostic kit, molecular biology, environmental and food sciences.

The preferred embodiments of the present invention have been disclosed. All modifications and alterations made by those familiar with the skill without departing from the spirits of the invention and appended claims and other embodiments shall remain within the protected scope and claims of the invention.

What is claimed is:

1. A method for analyzing a target substance in a sample, comprising the steps of:
    a) providing a magnetic material having its surface modified with recognizable molecules to capture a target substance in a sample;
    b) adding the magnetic material to the sample for the recognizable molecules thereon to capture the target substance in the sample;
    c) using a magnetic field to draw the magnetic material to the surface of an sensing region of an acoustics sensor to produce an acoustic effect thereon, wherein said surface of the sensing region has been modified with substances which can prevent non-specific binding; and
    d) converting the acoustic effect into the amount of the target substance in the sample.

2. The method according to claim 1, wherein the magnetic material includes magnetic particles, magnetic nanoparticles or superparamagnetic nanoparticles.

3. The method according to claim 1, wherein the recognizable molecules include compound, antigen, antibody, receptor, ligand, enzyme, protein, peptide, or nucleic acid.

4. The method according to claim 1, wherein the acoustic sensor includes quartz crystal microbalance (QCM), surface acoustic wave device, flexural plate wave sensor, acoustic plate mode device, or micro/nano cantilever beam.

5. The method according to claim 1, wherein the acoustic effect includes changes in deformation, changes in resonance frequency shift, or changes in acoustic wave signal.

6. The method according to claim 1, further comprising the use of an optical sensor to detect the magnetic material.

7. The method according to claim 6, wherein the surface of magnetic material further contains signal molecules having the properties of light absorption, fluorescence emission, phosphorescence emission, or luminescence emission.

8. The method according to claim 1, wherein the surface of magnetic material further contains signal molecules having the properties of light absorption, fluorescence emission, phosphorescence emission, or luminescence emission.

9. The method according to claim 2, wherein the recognizable molecules include compound, antigen, antibody, receptor, ligand, enzyme, protein, peptide, or nucleic acid.

* * * * *